US010184872B2

(12) United States Patent
Sakai

(10) Patent No.: US 10,184,872 B2
(45) Date of Patent: Jan. 22, 2019

(54) VISCOSITY/ELASTICITY MEASUREMENT DEVICE AND MEASUREMENT METHOD

(75) Inventor: Keiji Sakai, Tokyo (JP)

(73) Assignee: THE FOUNDATION FOR THE PROMOTION OF INDUSTRIAL SCIENCE, Tokyo (JP)

( * ) Notice: Subject to any disclaimer, the term of this patent is extended or adjusted under 35 U.S.C. 154(b) by 1065 days.

(21) Appl. No.: 14/113,288

(22) PCT Filed: May 11, 2012

(86) PCT No.: PCT/JP2012/062185
§ 371 (c)(1),
(2), (4) Date: Oct. 22, 2013

(87) PCT Pub. No.: WO2012/157572
PCT Pub. Date: Nov. 22, 2012

(65) Prior Publication Data
US 2014/0047903 A1     Feb. 20, 2014

(30) Foreign Application Priority Data

May 16, 2011   (JP) .............................. 2011-109833

(51) Int. Cl.
*G01N 11/14*     (2006.01)
(52) U.S. Cl.
CPC ........ *G01N 11/14* (2013.01); *G01N 2011/147* (2013.01)
(58) Field of Classification Search
CPC .......................... G01N 11/14; G01N 2011/147
(Continued)

(56) References Cited

U.S. PATENT DOCUMENTS 3,875,791 A * 4/1975 Fitzgerald .............. G01N 11/14
73/54.31
5,798,454 A    8/1998 Nakazeki et al.
(Continued)

FOREIGN PATENT DOCUMENTS

CN    1031279 A    2/1989
CN    1131984      9/1996
(Continued)

OTHER PUBLICATIONS

Machine translation of JP2007136443; Jun. 7, 2007.*
(Continued)

*Primary Examiner* — Peter Macchiarolo
*Assistant Examiner* — Alexander Mercado
(74) *Attorney, Agent, or Firm* — Hunton Andrews Kurth LLP

(57) ABSTRACT

A viscosity/elasticity measurement device includes a container for containing a measurement target material for detection of viscosity/elasticity is contained, a floating rotor made of material including a conductor, formed in a plate and circular shape when seen in plan view, and configured to be floated on a surface of the measurement target material, a magnet applying a magnetic field to the floating rotor in a direction perpendicular to a surface of the measurement target material, a rotational magnetic field control unit driving the magnet to apply a rotational magnetic field to the floating rotor, inducing an induction current in the conductor, and applying rotational torque to the floating rotor to rotate by Lorentz interaction between the induction current and the magnetic field applied to the floating rotor, and a viscosity detection unit detecting the viscosity/elasticity of the measurement target material based on a rotation state of the floating rotor.

19 Claims, 9 Drawing Sheets

(58) Field of Classification Search
USPC .............. 73/54.01, 61.51, 54.23–54.38
See application file for complete search history.

(56) References Cited

U.S. PATENT DOCUMENTS

| | | | |
|---|---|---|---|
| 5,821,407 A | 10/1998 | Sekiguchi et al. | |
| 6,499,336 B1* | 12/2002 | Raffer | G01N 11/14 73/54.23 |
| 2007/0059840 A1* | 3/2007 | Cohen | G01N 27/74 436/69 |
| 2011/0030454 A1* | 2/2011 | Laun | G01N 11/14 73/54.28 |
| 2011/0036150 A1* | 2/2011 | Sakai | G01N 11/14 73/54.31 |

FOREIGN PATENT DOCUMENTS

| | | |
|---|---|---|
| CN | 1737531 | 2/2006 |
| CN | 1890544 | 1/2007 |
| CN | 101506640 | 8/2009 |
| JP | 63-012936 | 1/1988 |
| JP | 2000-266117 | 9/2000 |
| JP | 2005-069872 | 3/2005 |
| JP | 2005055410 A | 3/2005 |
| JP | 2007-024744 | 2/2007 |
| JP | 2007083168 A | 4/2007 |
| JP | 2009-063505 | 3/2009 |
| WO | 02/076595 A1 | 10/2002 |
| WO | 2005/05753 | 6/2005 |
| WO | WO 2008022960 A1 * | 2/2008 ............ G01N 11/14 |
| WO | 2009/131185 | 10/2009 |

OTHER PUBLICATIONS

English translation of JP63012936; Jan. 20, 1988.*
English Translation of CN1031279A, Feb. 22, 1989.*
Office Action from related CN 201280023178.7 dated Sep. 3, 2014.
International Search Report dated Jun. 19, 2012 issued in corresponding PCT Application No. PCT/JP2012/062185 [With English Translation].
M. Bano et al., "A viscosity and density meter with a magnetically suspended rotor", Review of Scientific Instruments, Nov. 2003, vol. 74, No. 11, pp. 4788-4793.
T. Takamatsu et al., "Construction of a Rotating Cylinder Viscometer and Measurement of Intrinsic Viscosity of High Molecular Weight Polystyrenes", Toyo Soda Kenkyu Hokoku, 1976, vol. 20, No. 1, pp. 37-41.
German Office Action, issued in corresponding German Patent Application 112012002120.7, dated Feb. 24, 2015.
Japanese Office Action, issued in corresponding Japanese Patent Application 2011-109833, dated Apr. 7, 2015.
Chinese Office Action issued in Chinese Patent Application No. 20120023178.7, dated Nov. 25, 2015.
Notice of Allowance issued in corresponding Japanese Application No. 2011-109833, dated Oct. 6, 2015.

* cited by examiner

VISCOSITY/ELASTICITY MEASUREMENT DEVICE AND MEASUREMENT METHOD

FIELD OF THE INVENTION

The present invention relates to a viscosity/elasticity measurement device configured to measure viscosity and elasticity, which are mechanical properties of a material, and a measurement method thereof.

This application is a national stage application of International Application No. PCT/JP2012/062185, filed May 11, 2012, which claims priority to Japanese Patent Application No. 2011-109833, filed May 16, 2011, the content of which is incorporated herein by reference.

DESCRIPTION OF RELATED ART

In the conventional art, in order to detect mechanical properties of a target material, measurement of viscosity or elasticity is performed (for example, see Patent Document 1).

The measurement of viscosity and elasticity is a measurement technique necessary for quality management, performance evaluation, source material management, research and development in manufacturing processes of medicine, food, paint, ink, cosmetics, chemicals, paper, adhesives, fiber, plastic, beer, detergent, concrete admixtures, silicon, and so on.

The following methods are viscosity measurement methods known in the art.

(1) A viscosity pipe method; (2) a method using an oscillator to touch a sample; (3) a method using a surface acoustic wave; (4) a method using a rotor; (5) a method falling a sphere into a sample; (6) dynamic light scattering; (7) a Zimm type viscosity coefficient measurement method; and (8) an electromagnetically spinning (EMS) viscosity coefficient measurement method.

PRIOR ART DOCUMENT

Patent Document

Patent Document 1: Japanese Unexamined Patent Application, First Publication No. 2005-69872

SUMMARY OF THE INVENTION

Problems to be Solved by the Invention

However, in the above-mentioned methods, regarding methods (1) to (5), a large amount (several cc or more) of sample (a measurement target material) is needed.

In particular, in methods (2) to (5), a viscosity coefficient (a coefficient of viscosity) of the sample is required at least equal to 10 cP or more for highly precise measuring. For this reason, the methods (2) to (5) are impossible to accurately measure a viscosity coefficient of a material having a viscosity coefficient of less than 10 cP.

Further, regarding the method (6), a measurement device therefor is large. In addition, since the method (6) needs to transmit light such that measurement precision can be maintained, the method cannot be applied to materials other than the transparent samples.

In addition, regarding the method (7), a cylindrical rotor should be disposed in the sample in a vertically standing state.

However, in the method (7), when the rotor is maintained by buoyancy, since wettability of the rotor with respect to the sample is irregular, it is difficult to keep the rotor standing vertically by buoyancy. When the wettability of the rotor with respect to the sample is uneven in the entire surface of the rotor, it is impossible to stand the rotor vertically in the sample.

In addition, regarding the method (8), the rotor is rotated while the rotor comes in contact with a bottom of the container in which the rotor and the sample are contained. For this reason, friction occurs at a contact point between the rotor and the container, and an error occurs when a viscosity coefficient is measured.

Accordingly, regarding the method (8), like the methods (2) to (5), highly precise measurement is impossible when the sample having a viscosity coefficient of less than 10 cP due to the measurement error generated by the friction. In addition, the measurement error generated by the friction depends on a level of friction.

Further, regarding the method (8), in order to observe rotation of the rotor completely buried in the sample in the container, there is a need to pass the light therethrough such that the measurement precision can be maintained. For this reason, a sample other than the transparent sample, for example, a black sample, cannot be measured.

In addition, regarding the method (8), rotation of the rotor in the sample is observed using scattering of a laser. However, since a sample such as colloid, slurry, or the like, generates strongly scattered light as reflected light, the sample such as colloid, slurry, or the like, cannot be measured.

Further, regarding methods (7) and (8), a magnet that generates a rotational magnetic field is rotated along a sidewall of the container in which the sample is contained. For this reason, a region in which the magnet is rotated should be secured in an outer circumferential section of the sidewall of the container. Accordingly, when a temperature control device configured to control a sample temperature in the container, an electric field application device, or the like, is configured, the device is increased in size.

For the above-mentioned reasons, in the methods described in (1) to (8), it is difficult to simply measure a universal physical quantity, i.e., a mechanical physical quantity, such as viscosity and elasticity of a liquid or another soft material (a soft material or a soft matter) with a sample of a small amount. In addition, in the methods described in (1) to (8), it is difficult to perform highly precise measurement of the sample having a low viscosity coefficient. In addition, in the methods described in (1) to (8), miniaturization of the device is restricted.

In consideration of the above-mentioned circumstances, the present invention provides a viscosity/elasticity measurement device and a measurement method thereof that are capable of reducing an amount of sample, which is a measurement target material, in comparison with the conventional art, reducing the size of the device in comparison with the conventional art, and precisely measuring a viscosity coefficient of a material having a low viscosity of 10 cP or less in comparison with the conventional art.

Means for Solving the Problems

According to a first aspect of the present invention, a viscosity/elasticity measurement device includes: a container in which a measurement target material which is a target for detection of viscosity or elasticity is contained; a floating rotor made of material including a conductor, formed in a plate shape, having a circular shape when seen in plan view, and configured to be floated on a surface of the measurement target material; a magnet configured to apply a magnetic field to the floating rotor in a direction perpendicular to a surface of the measurement target material; a rotational magnetic field control unit configured to drive the magnet to apply a rotational magnetic field to the floating rotor, induce an induction current in the conductor in the floating rotor, and apply rotational torque to the floating rotor to rotate the floating rotor by Lorentz interaction between the induction current and the magnetic field applied to the floating rotor; and a viscosity detection unit configured to detect the viscosity or the elasticity of the measurement target material in contact with the floating rotor based on a rotation state of the floating rotor.

According to a second aspect of the present invention, in the viscosity/elasticity measurement device according to the first aspect, the magnet may be configured by a plurality of N poles and S poles alternately disposed in a disposition surface perpendicular to a rotation axis of the rotational magnetic field.

According to a third aspect of the present invention, in the viscosity/elasticity measurement device according to the second aspect, the magnet may be configured by a permanent magnet. And the magnet may generate the rotational magnetic field by rotating about the rotation axis in parallel to the disposition surface.

According to a fourth aspect of the present invention, in the viscosity/elasticity measurement device according to the second aspect, the magnet may be configured by electromagnets, and the rotational magnetic field control unit may generate the rotational magnetic field by driving electromagnets such that a disposed electromagnet has a different polarity from another electromagnet disposed adjacent.

According to a fifth aspect of the present invention, in the viscosity/elasticity measurement device according to any one of the first to fourth aspects, the magnet may be disposed at an upper section or a lower section of the container so as to be parallel to the surface of the measurement target material contained in the container.

According to a sixth aspect of the present invention, in the viscosity/elasticity measurement device according to any one of the first to fifth aspects, the floating rotor may be floated on the surface of the measurement target material by buoyancy, surface tension, or both buoyancy and surface tension.

According to a seventh aspect of the present invention, in the viscosity/elasticity measurement device according to any one of the first to sixth aspects, the floating rotor may have a rotational position-fixing section formed in a concave shape at a rotation center, and a protrusion may be formed in a direction parallel to the rotation axis may be inserted into the rotational position fixing section.

According to an eighth aspect of the present invention, in the viscosity/elasticity measurement device according to any one of the first to seventh aspects, the floating rotor may have a lower surface contacting the measurement target material and may be former in a substantially conical shape, an inner bottom surface of the container may have a planar shape, and a ratio between a thickness of a thickest portion and a thickness of a thinnest portion of the conical shape of the lower surface of the floating rotor may be set as a ratio such that a magnitude of shearing strain generated at the measurement target material in an interface between the lower surface of the floating rotor and the measurement target material is uniform when the floating rotor is rotated.

According to a ninth aspect of the present invention, in the viscosity/elasticity measurement device according to any one of the first to seventh aspects, the floating rotor may have a lower surface contacting with the measurement target material and is formed in a planar shape, an inner bottom surface of the container may have a substantially conical shape, and a ratio between a thickness of a thickest portion and a thickness of a thinnest portion of the substantially conical shape of the inner bottom surface of the container may be set as a ratio such that a magnitude of shearing strain generated at the measurement target material in an interface between the lower surface of the floating rotor and the measurement target material is uniform when the floating rotor is rotated.

According to a tenth aspect of the present invention, in the viscosity/elasticity measurement device according to any one of the first to ninth aspects, the device may further include a rotation detection unit configured to detect a revolution speed of the floating rotor, wherein the viscosity detection unit obtains the viscosity of the measurement target material from a ratio of the revolution speed of the rotational magnetic field and the revolution speed of the floating rotor.

According to an eleventh aspect of the present invention, in the viscosity/elasticity measurement device according to any one of the first to tenth aspects, the device may further include a standard data storage unit configured to previously store correspondence between a ratio between the revolution speed of the floating rotor and the rotational magnetic field in a plurality of reference materials having known viscosity coefficients, and the viscosity coefficients of the plurality of reference materials, as standard data. The ratio between the revolution speed of the floating rotor in the measurement target material measured by the viscosity detection unit and the rotational magnetic field may be compared with the standard data to obtain the viscosity of the measurement target material.

According to a twelfth aspect of the present invention, in the viscosity/elasticity measurement device according to the first to eleventh aspects, the device may further include a distance measurement unit configured to measure a sample distance between the lower surface of the floating rotor floated on the surface of the measurement target material and the bottom surface of the container; and a correction coefficient storage unit configured to show a relationship between the sample distance and the correction coefficient, wherein the viscosity detection unit reads the correction coefficient corresponding to the sample distance measured by the distance measurement unit from the correction coefficient storage unit, multiplies the correction coefficient by the viscosity obtained from the standard data, and outputs the multiplied result as the viscosity.

According to a thirteenth aspect of the present invention, in the viscosity/elasticity measurement device according to the tenth or eleventh aspect, the rotation detection unit may detect the revolution speed of the floating rotor through optical measurement.

According to a fourteenth aspect of the present invention, in the viscosity/elasticity measurement device according to any one of the first to thirteenth aspects, a mark may be added to an upper surface of the floating rotor, and the rotation detection unit may detect a revolution speed of the mark, and outputs the revolution speed of the mark as the revolution speed of the floating rotor.

According to a fifteenth aspect of the present invention, in the viscosity/elasticity measurement device according to any one of the first to fourteenth aspects, the measurement target material may be a liquid or a soft material.

According to a sixteenth aspect of the present invention, viscosity/elasticity measurement method includes: a process of containing a measurement target material which is a target for detection of viscosity or elasticity in a container; a process of disposing a floating rotor made of material including a conductor, formed in a plate shape, and having a circular shape when seen in plan view so as to be floated on the measurement target material, and applying a magnetic field to the floating rotor in a direction perpendicular to a surface of the measurement target material by a magnet; a process of driving the magnet so as to apply a rotational magnetic field to the floating rotor, inducing an induction current in the conductor of the floating rotor, and applying rotational torque to the floating rotor to rotate the floating rotor by Lorentz interaction of the induction current and the magnetic field applied to the floating rotor; and a process of detecting the viscosity or the elasticity of the measurement target material in contact with the floating rotor from the rotation state of the floating rotor.

Effects of the Invention

According to the above-mentioned viscosity/elasticity measurement device and the measurement method, the floating rotor is floated in the measurement target material, and the magnetic field parallel to the rotation axis of the floating rotor is applied to the floating rotor by the magnet. The magnetic field is rotated with respect to the rotation axis of the floating rotor to generate the rotational magnetic field, and the viscosity of the measurement target material is measured by the rotation state of the floating rotor. For this reason, in the above-mentioned viscosity/elasticity measurement device and the measurement method thereof, the floating rotor may be floated on the measurement target material, and the amount of measurement target material can be reduced in comparison with the conventional art.

In addition, according to the above-mentioned viscosity/elasticity measurement device and the measurement method, the magnetic field in the direction perpendicular to the upper surface of the measurement target material is applied, and the rotational magnetic field is generated by rotating the magnetic field. For this reason, there is no need to rotate the magnet in the outer circumferential section of the sidewall of the container, and there is no need to install the device configured to generate the rotational magnetic field in the outer circumferential section of the sidewall of the container. As a result, according to the above-mentioned viscosity/elasticity measurement device and the measurement method, there is room to install another device configuration in the outer circumferential section of the sidewall of the container, and the device can be reduced in size in comparison with the conventional art.

In addition, according to the above-mentioned viscosity/elasticity measurement device and the measurement method, the floating rotor does not come in contact with the bottom surface of the container. For this reason, the measurement error due to the contact between the rotor and the container as in the conventional measurement method is not generated. As a result, the viscosity/elasticity measurement device and the measurement method of the present invention can precisely perform the measurement of the viscosity coefficient of the material having the low viscosity of 10 cP or less in comparison with the conventional art.

DESCRIPTION OF EMBODIMENTS

<First Embodiment>

Figure 1:
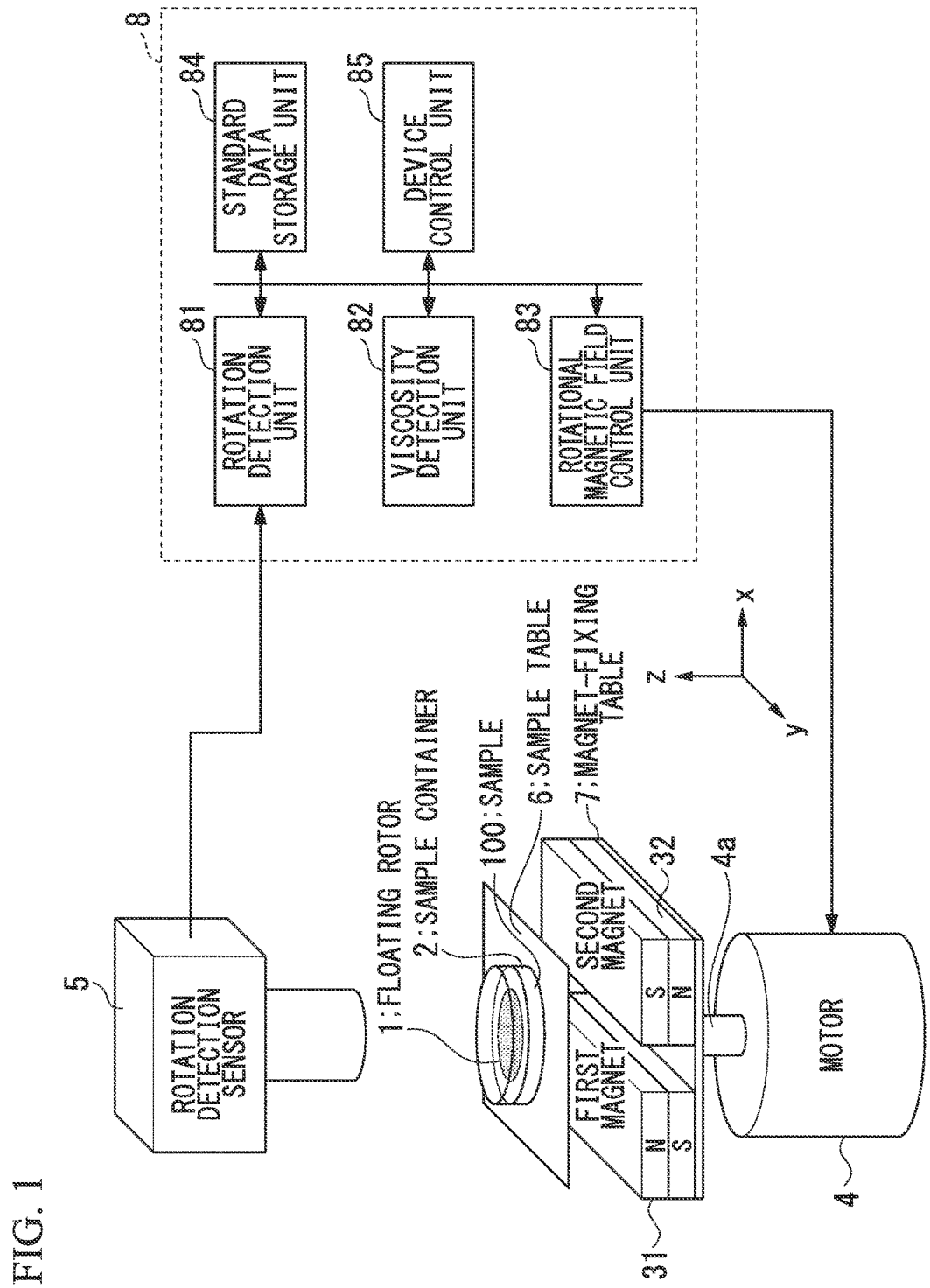
FIG. 1 is a view showing a configuration example of a viscosity/elasticity measurement device according to a first embodiment of the present invention.

Hereinafter, a first embodiment of the present invention will be described with reference to the accompanying drawings. FIG. 1 is a view showing a configuration example of a viscosity/elasticity measurement device according to the first embodiment of the present invention.

The viscosity/elasticity measurement device according to the embodiment includes a floating rotor 1, a sample container 2, a first magnet 31, a second magnet 32, a motor 4, a rotation detection sensor 5, a sample table 6, a magnet-fixing table 7 and a viscosity measurement unit 8. Hereinafter, the case in which a viscosity, i.e., a coefficient of viscosity, is measured as a mechanical property of a material by the viscosity/elasticity measurement device according to the first embodiment will be described. A viscosity described herein includes data, an index, or the like, showing a viscosity coefficient and viscosity. A measurement target material may be a liquid, slurry, or soft material. The soft material is, for example, a series of molecular material groups such as a macromolecule, a liquid crystal, a colloid, a biomolecule, and so on. In addition, the colloid is, for example, emulsions such as a milky liquid, an emulsion, a sol, and so on. Further, the biomolecule is, for example, a biological membrane, a protein, DNA, and so on.

The sample container 2 is a container in which a sample is contained as a measurement target material to measure a viscosity, which is a mechanical property. For example, a small schale and so on can be used as the sample container 2.

Figure 2:
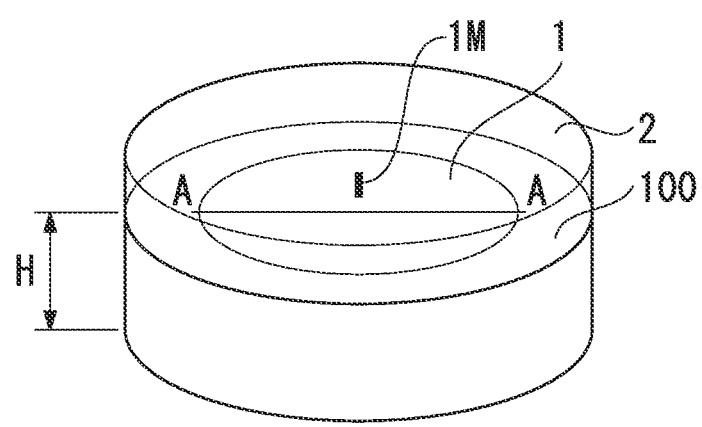
FIG. 2 is a conceptual view in which a sample 100 is contained in a sample container 2 and a floating rotor 1 is floated on a surface of the sample 100.

Next, FIG. 2 is a conceptual view in which a sample 100 is contained in the sample container 2 and the floating rotor 1 is floated on a surface of the sample 100. As shown in FIG. 2, an inner diameter of the sample container 2 may be slightly larger than a diameter of the floating rotor 1 floating in the sample 100. For example, the inner diameter of the sample container 2 has a size such that a distance from the floating rotor 1 may be maintained not to come in contact with an inner circumferential surface of the sample container 2 while the floating rotor 1 is being rotated. In addition, the sample 100 is contained at an amount corresponding to a depth H in the sample container 2. However, in the case of the embodiment, the depth H of the sample 100 contained in the sample container 2 may be set, for example, to H=about 0.5 mm, such that the floating rotor 1 does not come in contact with the bottom surface of the sample container 2.

For example, when a disc having a diameter of 10 mm is used as the floating rotor 1 and the sample 100 is contained in the container to a depth of H=0.5 mm, the sample 100 is about 300 µl. Even at this amount, according to the embodiment, measurement of the viscosity can be performed substantially precisely.

Accordingly, in comparison with the conventional art, the viscosity can be measured from an extremely small amount of sample 100.

The floating rotor 1 is floated on the surface of the sample 100 by buoyancy, surface tension, or both buoyancy and surface tension.

In addition, a mark 1M is added to an upper surface of the floating rotor 1, which is an opposite surface of a lower surface in contact with the sample 100. The mark may be a printed matter, a tape attachment, or a concave section or a convex section formed through machining of the upper surface as long as the mark can be detected by the rotation detection sensor 5.

FIGS. 3A to 3D are views showing configuration examples of the floating rotor 1. The floating rotor 1 shown in FIG. 3A has a disc (circular plate) shape, and the entire floating rotor 1 is formed of a lightweight conductor material such as aluminum or the like. That is, a material that forms the floating rotor 1 may be a conductor having a smaller specific gravity than the sample to be measured.

Figure 3A:
FIG. 3A is a view showing a configuration example of the floating rotor 1.
Figure 3B:
FIG. 3B is a view showing a configuration example of the floating rotor 1.

In addition, a sidewall 1B having a depth a is formed at an outer circumferential section of the disc (circular plate) of the floating rotor 1 shown in FIG. 3B. The floating rotor 1 having the above-mentioned configuration can be floated with respect to the sample 100 even when the conductor has a larger specific gravity than the sample to be measured. Accordingly, the material having a larger specific gravity than the sample to be measured can also be used as a material of the floating rotor 1.

Figure 3C:
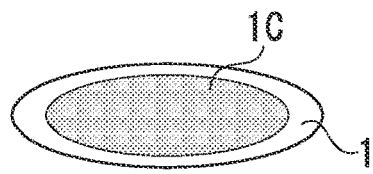
FIG. 3C is a view showing a configuration example of the floating rotor 1.
Figure 3D:
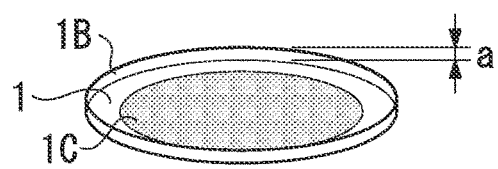
FIG. 3D is a view showing a configuration example of the floating rotor 1.

Further, FIGS. 3C and 3D are views showing configuration examples of the floating rotor 1, at least a portion of which is formed of a conductor.

While the floating rotor 1 shown in FIG. 3C has the same shape as the floating rotor 1 shown in FIG. 3A, only a portion of the floating rotor 1 is formed of a conductor such as aluminum or the like, and the other portion is formed of plastic, vinyl, or the like. For example, in FIGS. 3C and 3D, the conductor portion designated by reference sign 1C may be formed of a conductor such as aluminum or the like, and the other portion of the floating rotor 1 may be formed of an insulator. The conductor portion 1C may be configured by, for example, attaching a commercially released aluminum foil to the upper surface of the floating rotor 1.

Accordingly, an inexpensive floating rotor 1 can be easily formed from a circular plate such as a commercially released aluminum foil, a commercially released plastic, and so on. Then, a commercially released schale is used as the sample container 2. As a result, whenever the kind of the sample 100 of the measurement target is changed, the floating rotor 1 and the sample container 2 can be disposably used.

As a result, after the viscosity of the biomaterial is measured, when disposal of the biomaterial requires special attention, incineration processing or sterilization processing of the floating rotor 1 and the sample container 2 used in the measurement can be easily performed.

Figure 4A:
FIG. 4A is a view showing a cross-sectional shape of the floating rotor 1 taken along a line A-A of FIG. 1.
Figure 4B:
FIG. 4B is a view showing a cross-sectional shape of the floating rotor 1 taken along the line A-A of FIG. 1.

FIGS. 4A and 4B are views showing cross-sectional shapes of the floating rotor 1 taken along line A-A of FIG. 2. FIG. 4A shows an example of a cross-sectional structure of the floating rotor 1 having a circular plate shape when seen in plan view. FIG. 4B shows a cross-sectional structure of the floating rotor having a circular flat plate shape when seen in plan view, and a lower section, i.e., a lower surface in contact with the sample 100 having a substantially conical shape. When the lower surface of the floating rotor 1 is formed in a conical shape, a ratio between a thickness $a_{max}$ of the thickest portion of the floating rotor 1 and a thickness $a_{min}$ of the thinnest portion is set such that a magnitude of a shearing strain of the sample 100 is equal throughout the entire lower surface.

In addition, when the floating rotor 1 is formed in a shape shown in FIG. 4B, the bottom surface of the sample container 2 opposite to the conical lower surface of the floating rotor 1 in the sample container 2 is formed in a planar shape.

Meanwhile, when the floating rotor 1 is formed in a shape shown in FIG. 4A and the bottom surface of the sample container 2 opposite to the lower surface of the floating rotor 1, which is a planar surface, is formed in a substantially conical shape having a convex section directed toward the lower surface of the floating rotor 1, the shearing strain of the sample 100 in the entire lower surface of the floating rotor 1 can be uniformized like the floating rotor 1 shown in FIG. 4B.

Next, as shown in FIG. 1, the magnet-fixing table 7 is a flat plate-shaped member configured to fix a magnet that generates a rotational magnetic field. For example, the first magnet 31 and the second magnet 32 are fixed to the upper surface of the magnet-fixing table 7. The magnet-fixing table 7 is disposed in parallel to the surface of the sample 100 contained in the sample container 2. In addition, when the sample 100 is a liquid, the surface of the sample 100 is a liquid surface.

The first magnet 31 is disposed such that an S pole comes in contact with the upper surface side of the magnet-fixing table 7 and a surface opposite to the sample container 2 becomes an N pole.

The second magnet 32 is disposed such that an N pole comes in contact with the upper surface side of the magnet-fixing table 7 and a surface opposite to the sample container 2 becomes an S pole.

Accordingly, the first magnet 31 and the second magnet 32 are disposed such that the poles having different polarities are opposite to the sample container 2.

The first magnet 31 and the second magnet 32 are rectangular parallelepipeds, and disposed in parallel to each other.

The sample table 6 is a flat plate-shaped member configured to fix the sample container 2, in which the sample 100 is contained, and disposed such that the upper surface thereof is parallel to the upper surface of the magnet-fixing table 7.

Accordingly, the upper surface of the sample 100 contained in the sample container 2 is parallel to a planar surface formed by upper surfaces of the first magnet 31 and the second magnet 32 when the first magnet 31 and the second magnet 32 are rotated.

According to the disposition of the sample table 6, the magnet-fixing table 7, the first magnet 31 and the second magnet 3, as mentioned above, a magnetic field in a direction perpendicular to the upper surface of the floating rotor 1 put on the sample container 2 can be generated by the first magnet 31 and the second magnet 32. In addition, a magnetic field component perpendicular to the upper surface of the floating rotor 1 put on the sample container 2 may be generated.

The motor 4 is a drive mechanism configured to rotate the magnet-fixing table 7 in a rotation direction parallel to the surface of the magnet-fixing table 7. The motor 4 is fixed such that an axial direction of a rotary shaft 4a is perpendicular to the upper surface of the magnet-fixing table 7.

In addition, when seen in plan view, disposition of the sample container 2 and the motor 4 is set such that the rotary shaft 4a is disposed at a position at which the floating rotor 1 is rotated on the upper surface (the liquid surface) of the sample 100 with no contact with the inner wall of the sample container 2. That is, when seen in plan view, the sample container 2 and the motor 4 are disposed at a position at which the rotary shaft 4a overlaps a center of the sample container 2.

The rotation detection sensor 5 is disposed at a position in an upward direction of the sample container 2 as a position at which a mark (the mark 1M in FIG. 2) attached to the upper surface of the floating rotor 1 floated on the sample 100 in the sample container 2 can be detected, for example, optically detecting the mark. That is, the rotation detection sensor 5 emits a laser beam from a light radiation unit, and receives reflected light from the upper surface of the floating rotor 1 using a light receiving unit. Then, the rotation detection sensor 5 outputs a detected electrical signal corresponding to intensity of incident light. Here, when reflectance of the mark is larger than a reflectance of the upper surface of the floating rotor 1, a voltage of the detected electrical signal during a period in which the reflected light of the mark is received become higher. On the other hand, when the reflectance of the mark is smaller than the reflectance of the upper surface of the floating rotor 1, the voltage of the detected electrical signal during the period in which the reflected light of the mark is received is lowered.

In addition, an imaging device which is a microscope additionally having a lens and imaging elements such as a charge-coupled device (CCD), may be provided instead of the rotation detection sensor 5 and a captured image formed by enlarging and imaging the mark 1M may be output.

The viscosity measurement unit 8 includes a rotation detection unit 81, a viscosity detection unit 82, a rotational magnetic field control unit 83, a standard data storage unit 84 and a device control unit 85.

The rotation detection unit 81 detects the mark (1M of FIG. 2) of the floating rotor 1 by the detected electrical signal supplied from the rotation detection sensor 5, and outputs the detection number corresponding to the unit time (for example, one second) as a revolution speed (rpm: revolutions per minute) corresponding to the unit time. In addition, in mark detection, the rotation detection unit 81 may detect the mark 1M of the upper surface of the floating rotor 1 from the captured image imaged and output by the imaging device through image processing when the captured image of the imaging device is used, to obtain the revolution speed corresponding to the unit time, without using the detected electrical signal of the rotation detection sensor 5.

The rotational magnetic field control unit 83 performs rotation control of the motor 4 such that the motor 4 is rotated to a set revolution speed. Accordingly, the magnet-fixing table 7 is rotated via the rotary shaft 4a of the motor. According to the rotation of the magnet-fixing table 7, the magnetic field generated by the first magnet 31 and the second magnet 32 is rotated, and a rotational magnetic field configured to rotate the floating rotor 1 is generated.

A viscosity detection table showing a relationship between the revolution speed of the motor 4 and the revolution speed of the floating rotor 1 floated on the standard samples (the reference material) in which the viscosity coefficient is previously known, and the viscosity coefficient (cP) is stored in the standard data storage unit 84.

The viscosity detection table is drafted as follows. In the viscosity/elasticity measurement device of the embodiment, the standard sample having the previously known viscosity coefficient is contained in the sample container 2, and the floating rotor 1 is floated on the surface of the standard sample. Next, when the motor 4 is rotated at the plurality of preset revolution speeds $\Omega M$, the revolution speed $\Omega D$ of the floating rotor 1 corresponding to each of the revolution speeds $\Omega M$ of the motor 4 is measured by the above-mentioned rotation detection unit 81. Measurement of the revolution speed $\Omega D$ with respect to the standard sample is performed with respect to a plurality of the standard samples having different viscosities.

Figure 5:
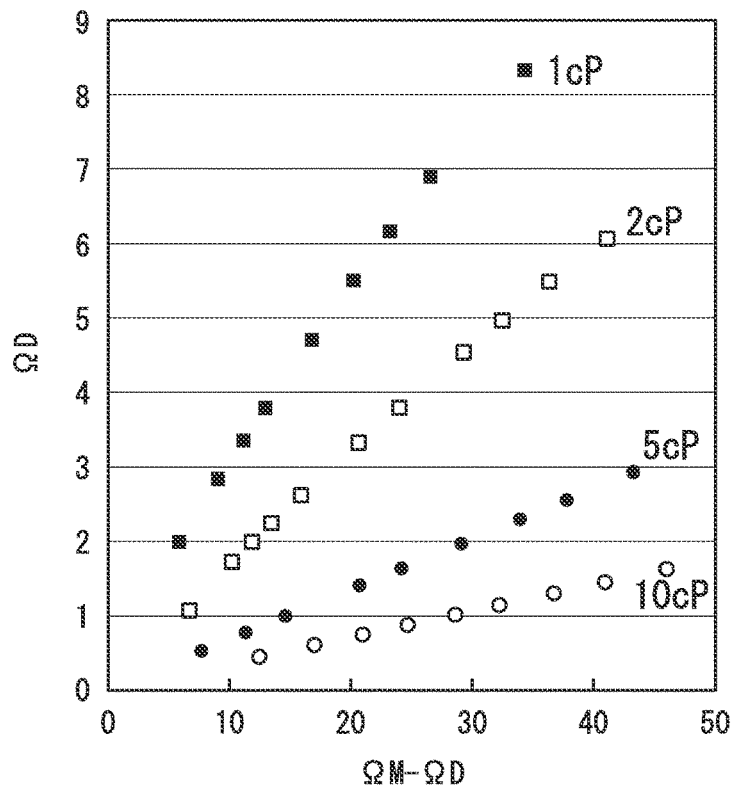
FIG. 5 is a view showing a relationship between a difference ($\Omega M - \Omega D$) between a revolution speed $\Omega M$ of a motor 4 and a revolution speed $\Omega D$ of a floating rotor, and the revolution speed $\Omega D$ of the floating rotor, in the standard samples having different viscosities.

FIG. 5 is a view showing a relationship between a difference ($\Omega M - \Omega D$) between the revolution speed $\Omega M$ of the motor 4 and the revolution speed $\Omega D$ of the floating rotor, and each of the revolution speeds $\Omega D$ of the floating rotor in the plurality of standard samples having the different viscosities. A horizontal axis is a rotation difference $\Omega MD$ ($\Omega M - \Omega D$) between the revolution speed $\Omega M$ and the revolution speed $\Omega D$, and a vertical axis is the revolution speed $\Omega D$. The viscosity coefficients of the respective used standard samples are different from each other, for example, 1 (cP), 2 (cP), 5 (cP) and 10 (cP). Then, a straight line showing a relationship between the rotation difference $\Omega MD$ and the revolution speed $\Omega D$ of each of the standard samples having different viscosity coefficients, i.e., correspondence of an inclination $\Omega D/\Omega MD$, is obtained from FIG. 5 through a least square method or the like. The inverse number of the inclination $\Omega MD/\Omega D$ is in proportion to the viscosity coefficient.

Figure 6:
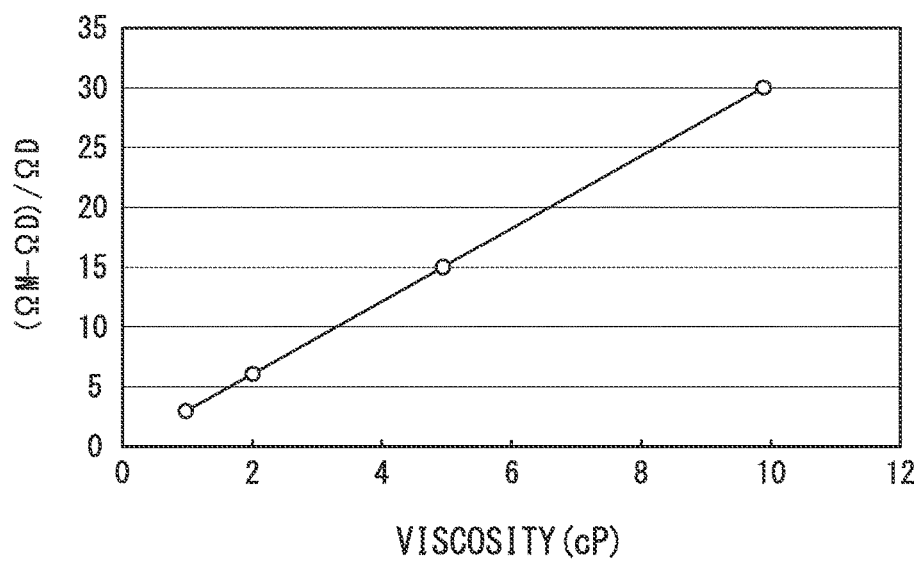
FIG. 6 is a view showing a relationship between a viscosity and an inverse number of an inclination $\Omega MD / \Omega D$.

Next, FIG. 6 is a view showing correspondence of the viscosity and the inverse number of the inclination $\Omega MD/\Omega D$.

Here, as shown in FIG. 1, the viscosity detection table showing the correspondence of the viscosity coefficient (cP)

and the inverse number of the inclination ΩMD/ΩD is stored in the standard data storage unit 84. In addition, an experimental equation, instead of the viscosity detection table, showing the correspondence between the viscosity coefficient (cP) and the inverse number of the inclination ΩMD/ΩD may be stored in the standard data storage unit 84.

The viscosity detection unit 82 controls the rotational magnetic field control unit 83 to operate the motor 4 rotating at the different revolution speeds ΩM. In addition, the viscosity detection unit 82 outputs a control signal to the rotation detection unit 81 whenever the revolution speed is changed.

The rotation detection unit 81 is received the revolution speed ΩD of the floating rotor 1 floated on the surface of the sample 100 contained in the sample container 2 at the revolution speed ΩM from the rotation detection sensor 5 whenever the control signal is supplied from the viscosity detection unit 82.

Then, the rotation detection unit 81 outputs the detected revolution speed ΩD to the viscosity detection unit 82 in accordance with the control signal.

The viscosity detection unit 82 calculates the inclination ΩD/ΩMD in the sample 100, and calculates the inverse number of the inclination ΩMD/ΩD, like the case of the above-mentioned standard sample. Here, ΩMD=ΩM−ΩD.

Then, the viscosity detection unit 82 reads the viscosity coefficient (cP) corresponding to the inverse number ΩMD/ΩD of the sample 100 from the viscosity detection table stored in the standard data storage unit 84, and outputs the viscosity coefficient as the viscosity of the sample 100. Here, when the experimental equation is stored in the standard data storage unit 84, the viscosity detection unit 82 reads the experimental equation from the standard data storage unit 84, and substitutes the inverse number of the inclination ΩMD/ΩD into the experimental equation, calculating the viscosity.

Figure 7:
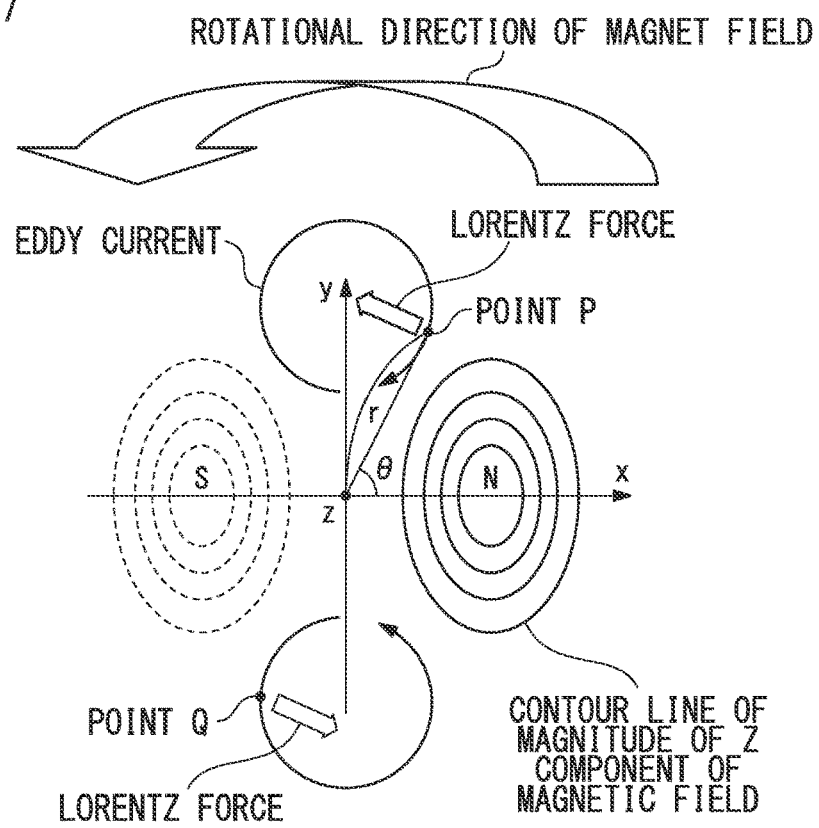
FIG. 7 is a conceptual view for describing a method of applying rotational torque to the floating rotor 1 by a rotational magnetic field generated as a first magnet 31 and a second magnet 32 are rotated.

Next, a method of applying rotational torque to the floating rotor 1 will be described with reference to FIG. 7. FIG. 7 is a conceptual view for describing a method of applying rotational torque to the floating rotor 1 by the rotational magnetic field generated through rotation of the first magnet 31 and the second magnet 32.

In FIG. 7, a magnetic field perpendicular to a certain reference surface is generated along the N pole of the first magnet 31 and the S pole of the second magnet 32. In the embodiment, the reference surface is the surface of the sample 100 contained in the sample container 2, and when the sample 100 is a liquid, the reference surface is a liquid surface.

The reference surface is a reference two-dimensional plane (the liquid surface of the sample 100) constituted by an x axis and a y axis. A rotary shaft of the floating rotor 1 rotated in the two-dimensional plane serves as a z axis.

Hereinafter, a z axis component of the magnetic field in the reference two-dimensional plane or at a neighboring point (x, y, z) is represented as Bz(x, y).

As described above, since the magnetic field is perpendicular to the reference two-dimensional plane, the magnetic field is assumed not to depend on the z axis. However, the following description still applies even when the magnetic field depends on the z axis. In addition, even though another component of the magnetic field not perpendicular to reference two-dimensional plane is presented, a component of a magnetic field perpendicular to the reference two-dimensional plane applies the rotational torque to the floating rotor 1 without causing failures.

FIG. 7 shows rotation of the first magnet 31 and the second magnet 32 observed from an axial component of the z axis in a positive (+) direction. When the magnet-fixing table 7 is rotated counterclockwise by the motor 4, a magnetic field Bz(x, y) is also rotated counterclockwise, and a rotational magnetic field in a counterclockwise direction is generated.

For example, a magnetic field when Bz(x, y)>0 in a half space x>0 and Bz(x, y)<0 in a half space x<0 is considered.

Here, in a half space y>0, a time variation ∂Bz/∂t of the magnetic field is positive (∂Bz/∂t>0). At the same time, in a half space y<0, a time variation ∂Bz/∂t of the magnetic field is negative (∂Bz/∂t<0).

Here, the floating rotor 1 disposed such that the upper surface thereof is on the reference two-dimensional plane (the liquid surface of the sample 100 contained in the sample container 2) or the upper surface thereof is near the reference two-dimensional plane and parallel to the reference two-dimensional plane when using the z axis as the rotary shaft is considered.

Here, when the rotational magnetic field is applied to the conductor in the floating rotor 1, according to Lenz's law, in the half space y>0, a clockwise eddy current flows in the conductor portion of the floating rotor 1. At the same time, in the half space y<0, a counterclockwise eddy current flows in the conductor portion of the floating rotor 1.

As described above, when the eddy current is generated in parallel to the reference two-dimensional plane, the magnetic field generated by the first magnet 31 and the second magnet 32 is perpendicular to the reference two-dimensional plane. For this reason, Lorentz force applied to the conductor of the floating rotor 1 by the eddy current and the magnetic field is generated in parallel to the reference two-dimensional plane.

Accordingly, in the reference two-dimensional plane, Lorentz force generated at an arbitrary point P in a region of x>0 and y>0 becomes FL1(Fx, Fy, 0). Here, Fx>0 and Fy>0.

In this case, in the reference two-dimensional plane, Lorentz force FL2(−Fx, −Fy, 0) is generated at an arbitrary point Q symmetrical to the z axis of the floating rotor 1 (the rotary shaft of the floating rotor 1) in a region of x<0 and y<0.

That is, forces acting on the points P and Q by Lorentz forces FL1(Fx, Fy, 0) and FL2(−Fx, −Fy, 0) become a couple of force.

As a result, rotational torque is applied to the conductor of the floating rotor 1, and the floating rotor 1 is rotated counterclockwise about the z axis of the rotation axis.

In addition, when the rotational magnetic field is rotated clockwise, a flow direction of the current in the eddy current is reversed from the case in which the above-mentioned rotational magnetic field is rotated counterclockwise, and the floating rotor 1 is also rotated clockwise.

Further, according to the rotation of the rotational magnetic field, in the reference two-dimensional plane, Lorentz force FL3(Fx, −Fy, 0) is applied to an arbitrary point in a region of x<0 and y>0.

In addition, in the reference two-dimensional plane, Lorentz force FL4(−Fx, Fy, 0) is applied to a point in a region of x<0 and y>0 where is symmetrical about the z axis with respect to an arbitrary point in a region x>0 and y<0. Accordingly, counterclockwise rotational torque with respect to the floating rotor 1 is generated by Lorentz force FL3 and Lorentz force FL4.

As described above, the magnetic field perpendicular to the reference two-dimensional plane generates the eddy current. A counterclockwise Lorentz force with respect to two points which is symmetrical about the z axis is generated by the rotational magnetic field and the eddy current through counterclockwise rotation of the magnetic field.

As a result, the eddy current generated at the conductor of the floating rotor 1 is entirely received the counterclockwise rotational torque and thereby the rotational torque is applied to the floating rotor 1 via the conductor.

A magnitude of the rotational torque applied to the floating rotor 1 is in proportion to a difference between the revolution speed ΩM of the rotational magnetic field and the revolution speed ΩD of the floating rotor 1. Here, the revolution speed ΩM of the rotational magnetic field is the same as the revolution speed of the motor 4.

Accordingly, the rotational torque is applied to the floating rotor 1 floated on the upper surface (surface) of the sample 100 contained in the sample container 2. As a result of application of the rotational torque, the floating rotor 1 is rotated in a direction in which the rotational torque is applied to the surface of the sample 100. When the revolution speed ΩD of the floating rotor 1 is constant, the revolution speed ΩD that becomes constant has a relationship in inverse proportion to the viscosity of the sample 100.

For example, for the purpose of simple description, a state in which a circular plate having a plane of a radius R is floated on the surface of the sample 100 contained in the sample container 2 and rotated as the floating rotor 1 is considered. Here, a distance between the lower surface of the floating rotor 1 and the inner bottom surface of the sample container 2 is d. Here, the floating rotor 1 is rotated such that the circular plate-shaped floating rotor 1 is parallel to the inner bottom surface of the sample container 2 by the rotational magnetic field generated based on a mechanism to which the above-mentioned rotational torque is applied.

In this case, a relationship showing Equation (1) representing the following Equation 1 is provided among the rotational torque T applied to the floating rotor 1, the revolution speed ΩD of the floating rotor 1, and a viscosity η of the sample 100.

[Equation 1]

$$T = \frac{\pi \eta \Omega_D R^4}{2d} \quad (1)$$

According to Equation (1), it will be appreciated that the viscosity η of the sample 100 is obtained by the rotational torque T applied to the floating rotor 1, the revolution speed ΩD of the floating rotor 1 floated and rotated on the surface of the sample 100, the radius R of the floating rotor 1, and a thickness (a depth) d of the sample 100 contained in the sample container 2.

Here, in measurement of the viscosity the rotational torque T applied to the floating rotor 1 is obtained in advance as a function of the revolution speed difference ΩMD between the revolution speed ΩM of the rotational magnetic field and the revolution speed ΩD of the floating rotor 1 as in FIG. 6 as described above by using the standard sample having the known viscosity η.

In addition, when the density of the sample 100 having the viscosity to be measured is known previously, an appropriate sample amount that has a depth d when it is contained in the sample container 2 having a conventional size to correspond to the density is weighted by a scale. Accordingly, the depth d of the sample 100 contained in the sample container 2 can be uniformized upon measurement of every sample 100 having different densities.

Further, when the sample 100 is contained in the sample container 2, a configuration for performing drop control of the sample 100 while measuring a height of the lower surface of the floating rotor 1 from the inner bottom surface of the sample container 2 may be used. Specifically, the drop control of the sample 100 is performed to drop the sample into the sample container 2 so as to become a height d (a distance d) obtained by the standard sample of FIG. 4 while measuring a height data by a liquid surface sensor. Here, a proper quantity mark may be added to the sidewall of the sample container 2 at a position of the distance d from the bottom surface. Then, a position between the proper quantity mark and the surface of the sample 100 may be detected by visual inspection or the above-mentioned liquid surface sensor, and the drop control of the sample 100 contained in the sample container 2 may be performed.

According to the above-mentioned first embodiment, an amount of the sample 100 which is a detection target material can be reduced in comparison with the conventional measurement. In addition, since the first magnet 31 and the second magnet 32 that generate the rotational magnetic field can be disposed in a downward direction of the sample container 2, the device can be reduced in size in comparison with the conventional art.

Further, according to the embodiment, the floating rotor 1 is floated on the surface of the sample 100. For this reason, a decrease in measurement precision due to contact between the floating rotor 1 and the sample container 2 can be prevented. As a result, the viscosity coefficient of the material having a low viscosity of about 10 cP or less can be more precisely measured in comparison with the conventional art.

An appropriate amount of sample 100 may be dropped into the sample container 2, and may detect the revolution speed of the floating rotor 1, the height d between the lower surface of the floating rotor 1 and the inner bottom surface of the sample container 2, and then, the viscosity of the sample 100 may be measured using these numerical values and Equation (1).

In addition, a combination of the first magnets 31 and the second magnets 32 in FIG. 1 is used for the magnet configured to generate the rotational magnetic field. In this case, the magnet generates the magnetic field by a set of one N pole and one S pole.

Figure 8:
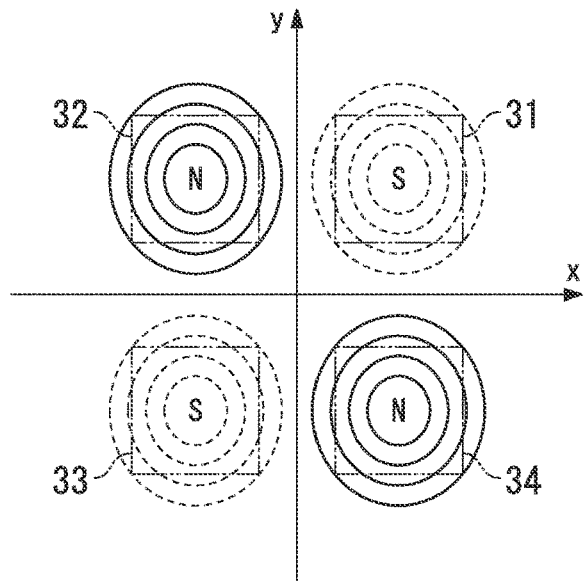
FIG. 8 is a view showing a state of a magnetic field when the first magnet 31, the second magnet 32, a third magnet 33 and a fourth magnet 34 are disposed on a magnet-fixing table 7 disposed in parallel to a reference two-dimensional plane.

Next, FIG. 8 is a view showing a state of the magnetic field when the first magnet 31, the second magnet 32, a third magnet 33 and a fourth magnet 34 are disposed on the magnet-fixing table 7 positioned in parallel to the reference two-dimensional plane.

In FIG. 8, in the reference two-dimensional plane, the first magnet 31 is disposed such that the S pole becomes the upper surface in the region of x>0 and y>0, the second magnet 32 is disposed such that the N pole becomes the upper surface in the region of x<0 and y>0, the third magnet 33 is disposed such that the S pole becomes the upper surface in the region of x<0 and y<0, and the fourth magnet 34 is disposed such that the N pole becomes the upper surface in the region of x>0 and y<0.

According to the disposition shown in FIG. 8, the magnetic field perpendicular to the reference two-dimensional plane is generated as described with reference to FIG. 7. Then, the rotational magnetic field can be applied to the conductor of the floating rotor 1, by rotating the magnet-fixing table 7. The rotational torque can be applied to the floating rotor 1 by the rotational magnetic field and the eddy current generated at the conductor of the floating rotor 1 by the rotational magnetic field.

As described above, the magnetic field may be generated using a combination of a plurality of N poles and S poles, for example, a combination of the two sets of N poles and S poles as shown in FIG. 8.

Figure 9:
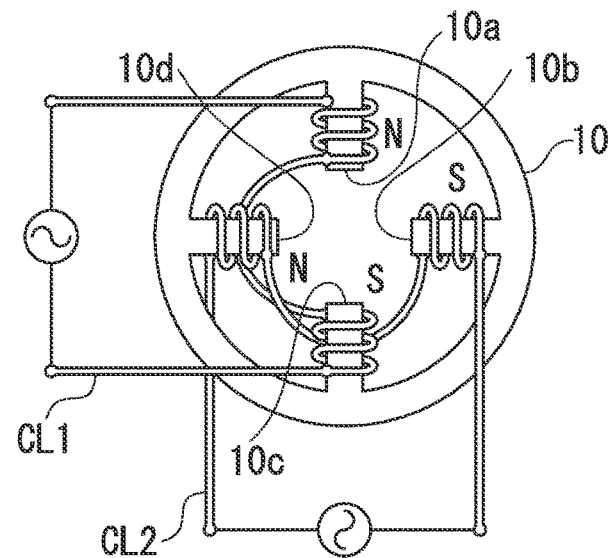
FIG. 9 is a view showing an electromagnet having a yoke 10 and teeth 10a, 10b, 10c and 10d protruding from the yoke 10 and disposed on the reference two-dimensional plane.

In addition, FIG. 9 is a view showing an electromagnet in which a yoke 10 and teeth 10a, 10b, 10c and 10d protruding from the yoke 10 are disposed on the reference two-dimensional plane. The electromagnet includes coils CL1 wound on the teeth 10a and the teeth 10c in different directions and coils CL2 wound on the teeth 10b and the teeth 10d in different directions.

Current flows through the coils CL1 and the coils CL2, and the magnetic field perpendicular to the reference two-dimensional plane is generated. Then, a direction of the flowing current may be periodically changed, and the magnetic field perpendicular to the reference two-dimensional plane may be rotated in order to form the rotational magnetic field.

In this case, in the rotational magnetic field control unit 83, the current flows through the coils CL1 and the coils CL2 of the electromagnet shown in FIG. 9, and the direction of the flowing current is periodically changed, generating the rotational magnetic field.

In addition, as described above, observation of the revolution speed of the floating rotor 1 is performed by detecting the mark 1M added to the upper surface of the floating rotor 1 using an imaging element such as an optical sensor, a CCD, or the like.

However, a configuration of optically measuring a variation in reflection and interference pattern due to radiation and rotation of a laser with respect to the upper surface of the floating rotor 1 may be provided.

In addition, a condenser may be configured such that a portion of the floating rotor 1 is substituted with a dielectric, and electrodes with the floating rotor 1 interposed therebetween are disposed so as to prevent interference with rotation of the magnet-fixing table 7 of FIG. 1 or the like. Then, when the dielectric, which is the mark, passes between the electrodes, the rotation detection unit 81 may detect a variation in capacity of the condenser constituted by the electrodes. Then, the number of variations in capacity of the condenser during a predetermined period (for example, one second) may be detected, and the revolution speed of the floating rotor 1 may be detected.

In addition, the rotational magnetic field control unit 83 may be configured such that the rotational period and the rotation direction of the rotational magnetic field applied to the floating rotor 1 are arbitrarily varied.

For example, as the rotation direction and the revolution speed of the rotational magnetic field are periodically swept, the rotational torque applied to the floating rotor 1 can be periodically changed.

Figure 10:
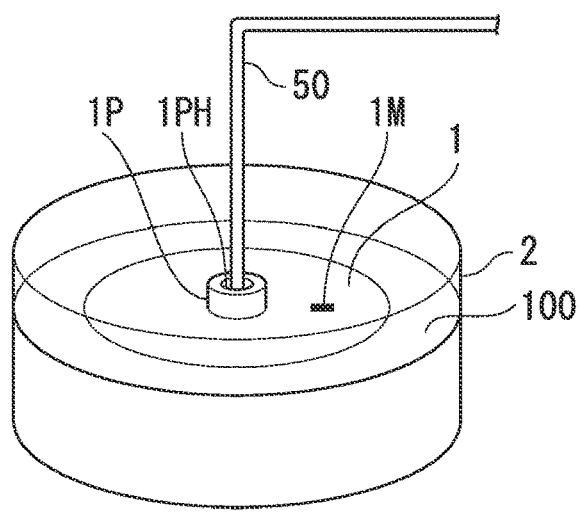
FIG. 10 is a view for describing a mechanism in which the floating rotor 1 is rotated in the sample container 2 with no contact with an inner circumferential surface of the sample container 2.

FIG. 10 is an illustration drawing for describing a mechanism in which the floating rotor 1 is rotated in the sample container 2 with no contact with the inner circumferential surface of the sample container 2.

As shown in FIG. 2, when the floating rotor 1 is rotated by applying the rotational magnetic field to the surface of the sample 100 in the sample container 2, the rotation axis of the floating rotor 1 may be deviated due to an application state of the rotational magnetic field. Here, when seen in plan view, when an inner area of the sample container 2 is set to be larger than an area of the floating rotor 1, even if the rotation axis of the floating rotor 1 is deviated, there is no contact with the sidewall in the sample container 2. However, when the sample container 2 is increased in size, the amount of the sample 100 required for measurement of the viscosity is increased.

For this reason, as shown in FIG. 10, a fixing section 1P having a convex shape projecting in a direction parallel to the rotation axis of the floating rotor 1 is formed at the upper surface of the floating rotor 1. The fixing section 1P has a groove 1PH formed at a center thereof and a fixed shaft 50 is inserted into the groove 1PH, thereby, the rotation mechanism in which the floating rotor 1 is rotatable is configured. The fixed shaft 50 is fixed to any one of the viscosity/elasticity measurement devices so as to be disposed to be parallel to the rotation axis of the floating rotor 1. The fixed shaft 50 substantially becomes the rotation axis of the floating rotor 1.

The floating rotor 1 can be rotated in a state in which a position of the rotation axis is kept by a predetermined place in the surface of the sample 100 contained in the sample container 2 by the fixing section 1P of the surface of the floating rotor 1 and the fixed shaft 50.

According to the configuration shown in FIG. 10, when seen in plan view, an internal size of the sample container 2 can be a minimum size needed to rotate the floating rotor 1 and measure the viscosity. As a result, the sample container 2 can be reduced in size in comparison with the conventional art, and the amount of the sample 100 needed to measure the viscosity can be reduced.

Next, measurement of elasticity using a viscosity/elasticity measurement device according to a second embodiment of the present invention will be described.

According to the viscosity/elasticity measurement device of the embodiment, the elasticity can be measured without requiring the viscosity as in the liquid. That is, according to the viscosity/elasticity measurement device of the embodiment, the viscosity coefficient and elastic modulus can be simultaneously measured with respect to the material having the elastic modulus such as gel, rubber, or the like, or the material such as a macromolecule solution in which the elastic modulus is generated by attenuation of the viscosity by displacement from a stop position when a certain torque is applied.

Here, the elastic modulus is a so-called spring constant, and corresponds to a recovering force in proportion to rotation deformation of the sample 100.

Figure 11:
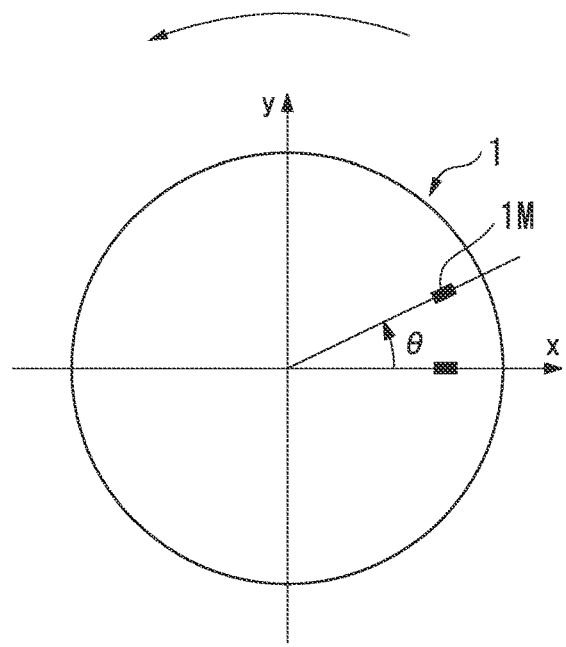
FIG. 11 is a view showing a rotation state of the floating rotor 1 when seen in plan view for describing elasticity measurement.

Accordingly, in case of the rubbery and viscous sample, the recovering force by the elastic modulus is increased in proportion to a level of distortion. For this reason, the floating rotor 1 starts to rotate and is stopped at a rotational angle θ at which the elastic force in proportion to the spring constant of the sample 100 is balanced with the rotational torque by the rotational magnetic field. FIG. 11 is a view showing a rotation state of the floating rotor 1 when seen in plan view for describing elasticity measurement. As the magnet-fixing table 7 is rotated counterclockwise, counterclockwise rotational torque is applied to the floating rotor 1 as described above.

Then, rotation of the floating rotor 1 is stopped at a position of the rotational angle θ at which the rotational torque applied to the floating rotor 1 and the repulsive force by the elasticity are balanced.

Here, the rotation detection unit 81 obtains the rotational angle θ from each of the captured images of the position of the mark 1M of the surface of the floating rotor 1 in a state in which the magnet-fixing table 7 is stopped while the motor 4 is not rotated and the position of the mark 1M when the rotation is stopped after the motor 4 is rotated at the predetermined revolution speed ΩM.

Figure 12:
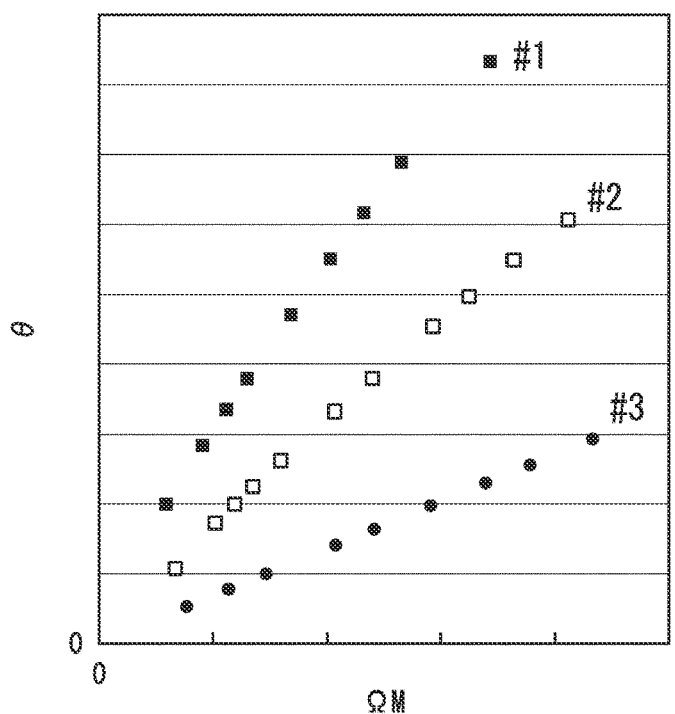
FIG. 12 is a view showing a relationship between a revolution speed $\Omega M$ of the motor 4 and a rotational angle $\theta$ at which the floating rotor 1 is stopped.

FIG. 12 is a view showing a relationship between a revolution speed ΩM of the motor 4, i.e., rotational torque, and a rotational angle θ at which the floating rotor 1 is stopped. In FIG. 12, a horizontal axis represents the revolution speed ΩM of the motor 4, and a vertical axis represents the rotational angle θ at which the floating rotor 1 is stopped.

That is, in the case of the viscosity/elasticity measurement device shown in FIG. 1, as the magnet-fixing table 7 is rotated by the motor 4, the first magnet 31 and the second magnet 32 disposed at the magnet-fixing table 7 generate the rotational magnetic field corresponding to the revolution speed of the motor 4.

Then, the rotational magnetic field control unit 83 changes the revolution speed of the motor 4 according to previously set steps, obtains the rotational angle θ at every revolution speed, calculates the relationship between the revolution speed ΩM and the rotational angle θ, and drafts a graph shown in FIG. 12. Here, the above-mentioned processing is performed to a plurality of standard samples in which the elasticity is previously determined, like the case of the viscosity, in order to obtain a standard data using for the elasticity measurement of the sample 100 having an unknown elasticity. Like the case of obtaining the standard data of the viscosity, the standard sample is contained in the sample container 2, and the above-mentioned rotational angle θ is measured.

Figure 13:
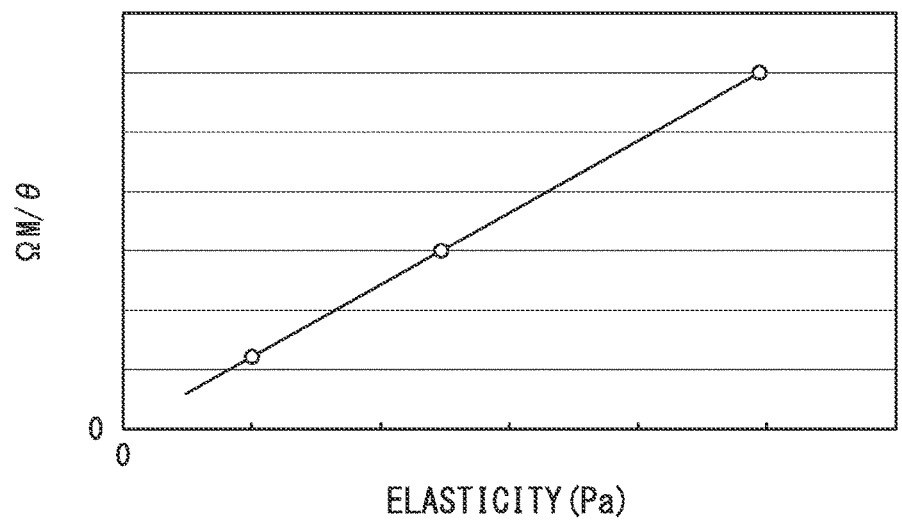
FIG. 13 is a view showing a relationship between the elasticity and a ratio between a revolution speed and a rotational angle.

FIG. 13 is a view showing a relationship between the elasticity and a ratio between the revolution speed and the rotational angle. In FIG. 13, a horizontal axis represents the elasticity (the elastic modulus: Pa), and a vertical axis represents a proportionality coefficient between the revolution speed ΩM and the rotational angle θ. Here, the viscosity is in inverse proportion to the rotational angle θ.

FIG. 13 shows standard data of the elasticity using for the elasticity measurement, which is obtained by matching the inclination of each standard sample in FIG. 12, i.e., a ratio between the revolution speed ΩM and the rotational angle θ, with the viscosity of the corresponding standard sample.

In measurement of the sample 100 of the actually unknown elasticity, the sample 100 of the measurement target is contained in the sample container 2, and the rotational magnetic field control unit 83 controls the motor 4 to rotate at a preset revolution speed like the case of the standard sample.

Then, the rotation detection unit 81 obtains the rotational angle θ at every revolution speed, and outputs the rotational angle θ to the viscosity detection unit 82.

The viscosity detection unit 82 obtains the proportionality coefficient between the revolution speed ΩM and the rotational angle θ supplied from the rotation detection unit 81. Data of the elasticity corresponding to the proportionality coefficient is read from the standard data of the standard data storage unit 84, and the read data is output as the elasticity of the sample 100.

In addition, as the rotational torque applied to the floating rotor 1 is varied by time, the elasticity and the viscosity can be simultaneously measured. In this case, the magnet that generates the rotational magnetic field is constituted by the electromagnet shown in FIG. 9.

For example, after the excitation current is applied to the electromagnet to apply the predetermined rotational torque with respect to the floating rotor 1, application of the excitation current is stopped, and the rotation state of the floating rotor 1 after stoppage is observed.

Here, the floating rotor 1 causes rotational oscillation according to the elasticity of the sample 100. Here, a period and an oscillation time of the rotational oscillation are in proportion to the elasticity, and a damping ratio of an amplitude of the rotational oscillation is in proportion to the viscosity.

Accordingly, the damping ratio of the amplitude, the period and the oscillation time of the rotational oscillation are measured by applying the rotational magnetic field to the floating rotor 1 at each of the plurality of standard samples having the previously known viscosity and elasticity, and the standard data is obtained and is previously stored in the standard data storage unit 84.

Next, when the measurement target material having the actually unknown viscosity and elasticity is measured, the viscosity detection unit 82 measures the damping ratio of the amplitude, the period and oscillation time of the sample 100 which is the measurement target material, and reads the viscosity corresponding to the damping ratio of the measured amplitude and the elasticity corresponding to the period and the oscillation time from the standard data.

Then, the viscosity detection unit 82 outputs the viscosity and the elasticity read from the standard data as the viscosity and the elasticity of the sample 100 of the measurement target.

As described above, according to the embodiment, the viscosity and the elasticity of the sample 100 can be simultaneously measured.

In addition, as the rotation direction and the rotational torque of the rotational magnetic field applied to the floating rotor 1, i.e., the revolution speed ΩM of the motor 4, are periodically swept, the rotational torque can be periodically applied to the floating rotor 1.

Then, while varying the period of sweeping the rotation direction and the rotational torque, as the amplitude and phase of the rotational oscillation of the floating rotor 1 are observed by the captured image, the viscosity and the elasticity can be independently measured.

That is, as described above, observation of the rotational oscillation is to detect the damped oscillation after elimination of the magnetic field as a frequency spectrum, and theoretically the same as measurement of the viscosity and the elasticity after elimination of the magnetic field.

EXAMPLE

Next, a specific application example of the viscosity/elasticity measurement device (the mechanical property measurement device) according to the first embodiment shown in FIG. 1 will be described.

A glass scale having an inner diameter of 35 mm and an inner sidewall with a height of 10 mm was used as the sample container 2. Then, 3 cc of the sample 100 which was the measurement target material was contained in the sample container 2. A temperature of the sample 100 was 20° C.

As shown in FIG. 5, four kinds of viscosity coefficients 1 cP, 2 cP, 5 cP and 10 cP were used as the standard samples having previously known viscosities.

Then, an aluminum disc having a diameter of 30 mm and a thickness of 0.1 mm was used as the floating rotor 1 rotated on the surface of the standard sample.

Next, the rotational magnetic field control unit 83 drove the motor 4 to rotate the magnet-fixing table 7.

As a result, the first magnet 31 and the second magnet 32 were rotated. A magnetic field perpendicular to the liquid surface of the standard sample contained in the sample container 2 was generated by the rotation of the first magnet 31 and the second magnet 32, and the magnetic field was rotated to generate a rotational magnetic field. Rotational torque was applied to the floating rotor 1 by the rotational magnetic field, and the floating rotor 1 was rotated in the same direction as the rotation direction of the applied rotational magnetic field.

Then, the rotation detection unit 81 stored a moving image of the rotation of the floating rotor 1 imaged by, for example, the rotation detection sensor (the imaging element) 5 in the storage unit of the rotation detection unit 81 as the captured image, and obtained a rotational period of the mark 1M through image processing. The rotation detection unit 81 obtained the revolution speed of the floating rotor 1 from the rotational period of the mark 1M.

Whenever the revolution speed $\Omega M$ of the motor 4 changed, the corresponding revolution speed $\Omega D$ of the floating rotor 1 was obtained. Then, as shown in FIG. 5, at every standard sample having different viscosities, correspondence between the revolution speed $\Omega D$ of the floating rotor 1 and the difference ($\Omega M - \Omega D$) between the revolution speeds $\Omega M$ and $\Omega D$ was obtained.

In FIG. 5, a straight line showing the relationship between the revolution speed $\Omega D$ of the floating rotor 1 of each standard sample and the difference between the revolution speeds $\Omega M$ and $\Omega D$ passes through an origin (0). For this reason, FIG. 5 shows that the viscosity can be obtained using only the relationship between the revolution speed of the floating rotor 1 and the rotational torque applied to the floating rotor 1.

As a result, a straight line showing the correspondence between the viscosity and a ratio between the revolution speed $\Omega D$ and the difference between the revolution speeds $\Omega M$ and $\Omega D$ shown in FIG. 6 also passes through the origin. Accordingly, as the standard data is used, the viscosity can be accurately measured.

In addition, a program for realizing a function of the viscosity measurement unit 8 as shown in FIG. 1 may be recorded in a computer-readable recording medium, the program recorded in the recording medium may be read by a computer system, and the measurement of the viscosity and the elasticity may be performed by executing the program. In addition, the "computer system" used herein includes an operating system (OS) or a hardware such as peripheral devices or the like.

Further, the "computer system" includes a homepage providing environment or display environment when a World Wide Web (WWW) system is used.

In addition, the "computer-readable recording medium" refers a portable medium such as a flexible disk, a magneto-optical disc, a ROM, a CD-ROM, or the like, and a storage device such as a hard disk or the like installed in the computer system. Further, the "computer-readable recording medium" includes a medium that dynamically holds a program for a short time such as a communication wire when the program is transmitted through a network such as the Internet or the like, or a communication line such as a telephone line or the like. In addition, the "computer-readable recording medium" includes a memory that can hold the program for a certain period such as a volatile memory in the computer system that becomes a server or a client of this case. In addition, the program may realize some of the above-mentioned functions. Further, the program may be realized in combination with a program having the above-mentioned functions and recorded in the computer system.

Hereinabove, while the embodiment of the present invention has been described with reference to the accompanying drawings, a specific constitution is not limited to the embodiment but may include designs or the like without departing from the spirit of the present invention.

INDUSTRIAL APPLICABILITY

According to the above-mentioned description, in the viscosity/elasticity measurement, the sample amount can be reduced in comparison with the conventional art, and the device can be reduced in size in comparison with the conventional art. In addition, according to the above-mentioned description, it is possible to provide the viscosity/elasticity measurement device and the measurement method thereof that are capable of more precisely measuring the viscosity coefficient of the material having a low viscosity of about 10 cP or less than the conventional art. Accordingly, a range of the sample that enables measurement of the viscosity coefficient/elasticity is increased, and measurement precision can be improved.

DESCRIPTION OF REFERENCE NUMERALS

1: floating rotor
1M: mark
2: sample container
31: first magnet
32: second magnet
4: motor
4a: rotary shaft
5: rotation detection sensor
6: sample table
7: magnet-fixing table
8: viscosity measurement unit
81: rotation detection unit
82: viscosity detection unit
83: rotational magnetic field control unit
84: standard data storage unit
100: sample (measurement target material)

The invention claimed is:

1. A viscosity/elasticity measurement device comprising:
  a container in which a measurement target material which is a target for detection of a viscosity or an elasticity is contained;
  a floating rotor comprising a conductor formed in a plate shape, the floating rotor having a circular shape when seen in a plan view, and configured to be floated on a surface of the measurement target material by one or more of the group consisting of buoyancy and surface tension without contacting an inner bottom surface of the container;
  a magnet configured to apply a magnetic field to the floating rotor in a direction perpendicular to an upside surface of the floating rotor floated on the surface of the measurement target material;
  a rotational magnetic field control unit configured to drive the magnet to apply a rotational magnetic field to the floating rotor, induce an induction current in the conductor in the floating rotor, and apply rotational torque to the floating rotor to rotate the floating rotor by Lorentz interaction between the induction current and the magnetic field applied to the floating rotor; and
  a viscosity detection unit configured to detect the viscosity or the elasticity of the measurement target material in contact with the floating rotor based on a rotation state of the floating rotor, wherein
  the floating rotor is rotated while floating on the surface of the measurement target material without contacting the container by the rotational torque due to Lorentz interaction between the induction current and the magnetic field applied to the floating rotor.

2. The viscosity/elasticity measurement device according to claim 1, wherein the magnet is configured by a plurality of N poles and S poles alternately disposed in a disposition surface perpendicular to a rotation axis of the rotational magnetic field.

3. The viscosity/elasticity measurement device according to claim 2, wherein the magnet is configured by a permanent magnet, the magnet configured to be rotated about the rotation axis and parallel to a disposition surface direction so as to generate the rotational magnetic field.

4. The viscosity/elasticity measurement device according to claim 2, wherein the magnet is configured by electromagnets, and
the rotational magnetic field control unit is configured to generate the rotational magnetic field by driving electromagnets such that a disposed electromagnet has a different polarity from another electromagnet disposed adjacent.

5. The viscosity/elasticity measurement device according to claim 1, wherein the magnet is disposed at an upper section or a lower section of the container so as to be parallel to the surface of the measurement target material contained in the container.

6. The viscosity/elasticity measurement device according to claim 1, wherein the floating rotor has a rotational position-fixing section formed in a concave shape at a rotation center on the upside surface of the floating rotor, and
a protrusion formed in a direction parallel to the rotation axis is inserted into the rotational position fixing section.

7. The viscosity/elasticity measurement device according to claim 1, wherein
the floating rotor has a lower surface contacting with the measurement target material and is formed in a substantially conical shape,
an inner bottom surface of the container has a planar shape, and
a ratio between a thickness of a thickest portion and a thickness of a thinnest portion of the conical shape of the lower surface of the floating rotor is set as a ratio such that a magnitude of shearing strain generated at the measurement target material in an interface between the lower surface of the floating rotor and the measurement target material is uniform when the floating rotor is rotated.

8. The viscosity/elasticity measurement device according to claim 1, wherein
the floating rotor has a lower surface contacting with the measurement target material and is formed in a planar shape,
the inner bottom surface of the container has a substantially conical shape, and
a ratio between a thickness of a thickest portion and a thickness of a thinnest portion of the substantially conical shape of the inner bottom surface of the container is set as a ratio such that a magnitude of shearing strain generated at the measurement target material in an interface between the lower surface of the floating rotor and the measurement target material is uniform when the floating rotor is rotated.

9. The viscosity/elasticity measurement device according to claim 1, further comprising a rotation detection unit configured to detect a revolution speed of the floating rotor,
wherein the viscosity detection unit obtains the viscosity of the measurement target material from a ratio of the revolution speed of the rotational magnetic field and the revolution speed of the floating rotor.

10. The viscosity/elasticity measurement device according to claim 1, further comprising
a standard data storage unit configured to previously store correspondence between a ratio between the revolution speed of the floating rotor and the rotational magnetic field in a plurality of reference materials having known viscosity coefficients, and the viscosity coefficients of the plurality of reference materials, as standard data,
wherein the standard data storage unit obtains the viscosity of the measurement target material by comparing the ratio between the revolution speed of the floating rotor in the measurement target material measured by the viscosity detection unit and the rotational magnetic field with the standard data.

11. The viscosity/elasticity measurement device according to claim 10, further comprising:
a distance measurement unit configured to measure a sample distance between a lower surface of the floating rotor floated on the surface of the measurement target material and the bottom surface of the container by using a liquid surface sensor;
wherein the viscosity detection unit, multiplies a correction coefficient by the viscosity obtained from the standard data, and outputs the multiplied result as the viscosity, the correction coefficient corresponding to the sample distance measured by the distance measurement unit.

12. The viscosity/elasticity measurement according to claim 9, wherein the rotation detection unit detects the revolution speed of the floating rotor through optical measurement.

13. The viscosity/elasticity measurement device according to claim 1, wherein a mark is added to an upper surface of the floating rotor, and
the rotation detection unit detects a revolution speed of the mark, and outputs the revolution speed of the mark as the revolution speed of the floating rotor.

14. The viscosity/elasticity measurement device according to claim 1, wherein the measurement target material is a liquid or a soft material.

15. A viscosity/elasticity measurement method comprising:
a process of containing a measurement target material which is a target for detection of viscosity or elasticity in a container;
a process of disposing a floating rotor on a surface of the measurement target material, the floating rotor configured to be floated on the surface of the measurement target material by one or more of the group consisting of buoyancy and surface tension by one or more of the group consisting of buoyancy and surface tension without contacting an inner bottom surface of the container, the floating rotor comprising a conductor formed in a plate shape, the floating rotor having a circular shape when seen in a plan view, and applying a magnetic field to the floating rotor in a direction perpendicular to an upside surface of the floating rotor floated on the surface of the measurement target material by a magnet;
a process of driving the magnet so as to apply a rotational magnetic field to the floating rotor, inducing an induction current in the conductor of the floating rotor, and applying rotational torque to the floating rotor so as to rotate the floating rotor by Lorentz interaction of the induction current and the magnetic field applied to the floating rotor; and a process of detecting the viscosity or the elasticity of the measurement target material contacted with the floating rotor from the rotation state of the floating rotor, wherein the floating rotor is rotated while floating on the surface of the measurement target material without contacting the container by the rotational torque due to Lorentz interaction between the induction current and the magnetic field applied to the floating rotor.

16. The viscosity/elasticity measurement device according to claim 1, wherein the floating rotor is made of the conductor having a smaller specific gravity than a sample to be measured.

17. The viscosity/elasticity measurement device according to claim 1, wherein the floating rotor has a side wall formed at an outer circumferential section of the floating rotor.

18. The viscosity/elasticity measurement device according to claim 1, wherein the floating rotor has a circular plate shape.

19. The viscosity/elasticity measurement device according to claim 1, further comprising a viscosity detection unit configured to determine a viscosity of the measurement target material, wherein the viscosity detection unit determines the viscosity of the measurement target material by a following equation, $$T = \frac{\pi \eta \Omega_D R^4}{2d}$$

where T denotes the rotational torque applying to the floating motor, $\eta$ denotes the viscosity of the measurement target material, $\Omega_D$ denotes a revolution speed of the floating rotor, R denotes a radius of the floating rotor, and d denotes a depth of the measurement target material contained in the container.

* * * * *